United States Patent [19]

Sholder

[11] Patent Number: 5,222,493
[45] Date of Patent: Jun. 29, 1993

[54] VERIFICATION OF CAPTURE USING AN INDIFFERENT ELECTRODE MOUNTED ON THE PACEMAKER CONNECTOR TOP

[75] Inventor: Jason A. Sholder, Northridge, Calif.

[73] Assignee: Siemens Pacesetter, Inc., Sylmar, Calif.

[21] Appl. No.: 590,989

[22] Filed: Oct. 1, 1990

[51] Int. Cl.⁵ .............................. A61N 1/362
[52] U.S. Cl. .................... 128/419 P; 128/419 PG
[58] Field of Search ........ 128/419 P, 419 R, 419 PT, 128/419 PG, 419 PS

[56] References Cited

U.S. PATENT DOCUMENTS

| | | | |
|---|---|---|---|
| 3,920,024 | 11/1975 | Bowers | 128/419 PG |
| 4,310,000 | 1/1982 | Lindemans | 128/419 PG |
| 4,549,548 | 10/1985 | Wittkampf et al. | 128/419 PG |
| 4,585,004 | 4/1986 | Brownlee | 128/419 PT |
| 5,018,523 | 5/1991 | Bach, Jr. et al. | 128/786 |

Primary Examiner—Kyle L. Howell
Assistant Examiner—Kennedy J. Schaetzle
Attorney, Agent, or Firm—Leslie S. Miller

[57] ABSTRACT

A cardiac pacing system includes circuitry for verification of capture having an indifferent electrode mounted on the pacemaker connector top. The cardiac pacing system may use one or two bipolar or unipolar leads. Capture is sensed between the indifferent electrode and one of the electrodes on the lead or leads. Either electrode on the lead or leads can be used as the other electrode forming a sensing pair with the indifferent electrode. The electrode is located in the plastic connector top portion of the implanted pacemaker, and may be disposed at a side of the pacemaker, when implanted, facing the interior of the patient, or facing the exterior of the patient.

7 Claims, 11 Drawing Sheets

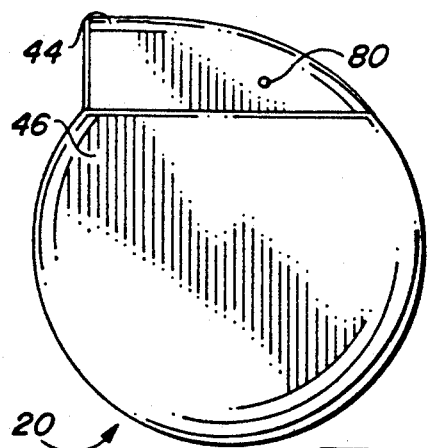
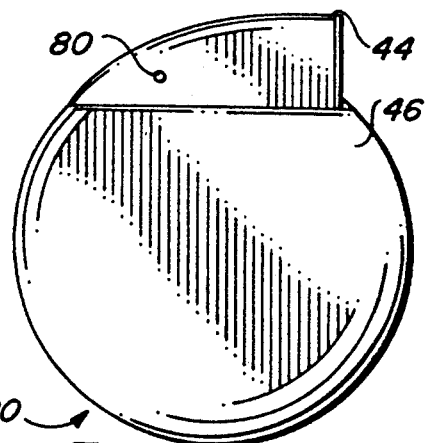
FIG. 2  FIG. 3
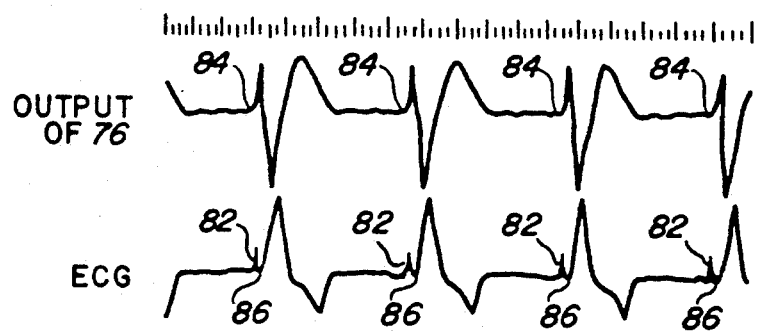
FIG. 4
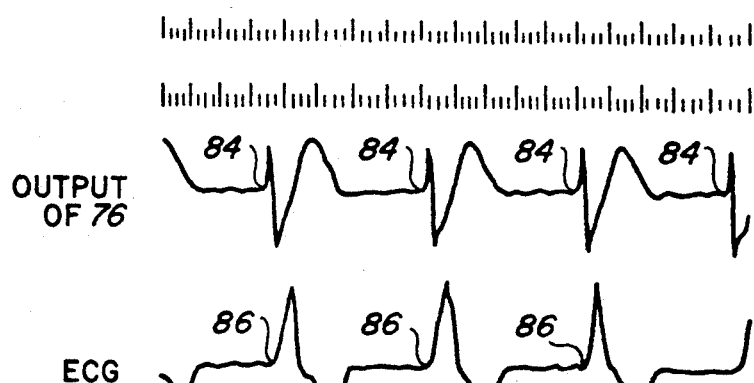
FIG. 5
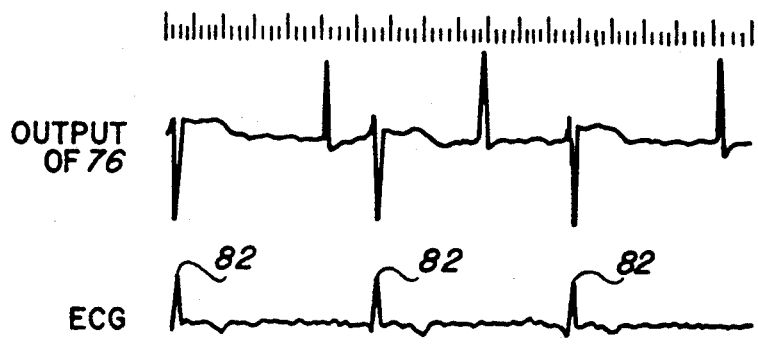
FIG. 6

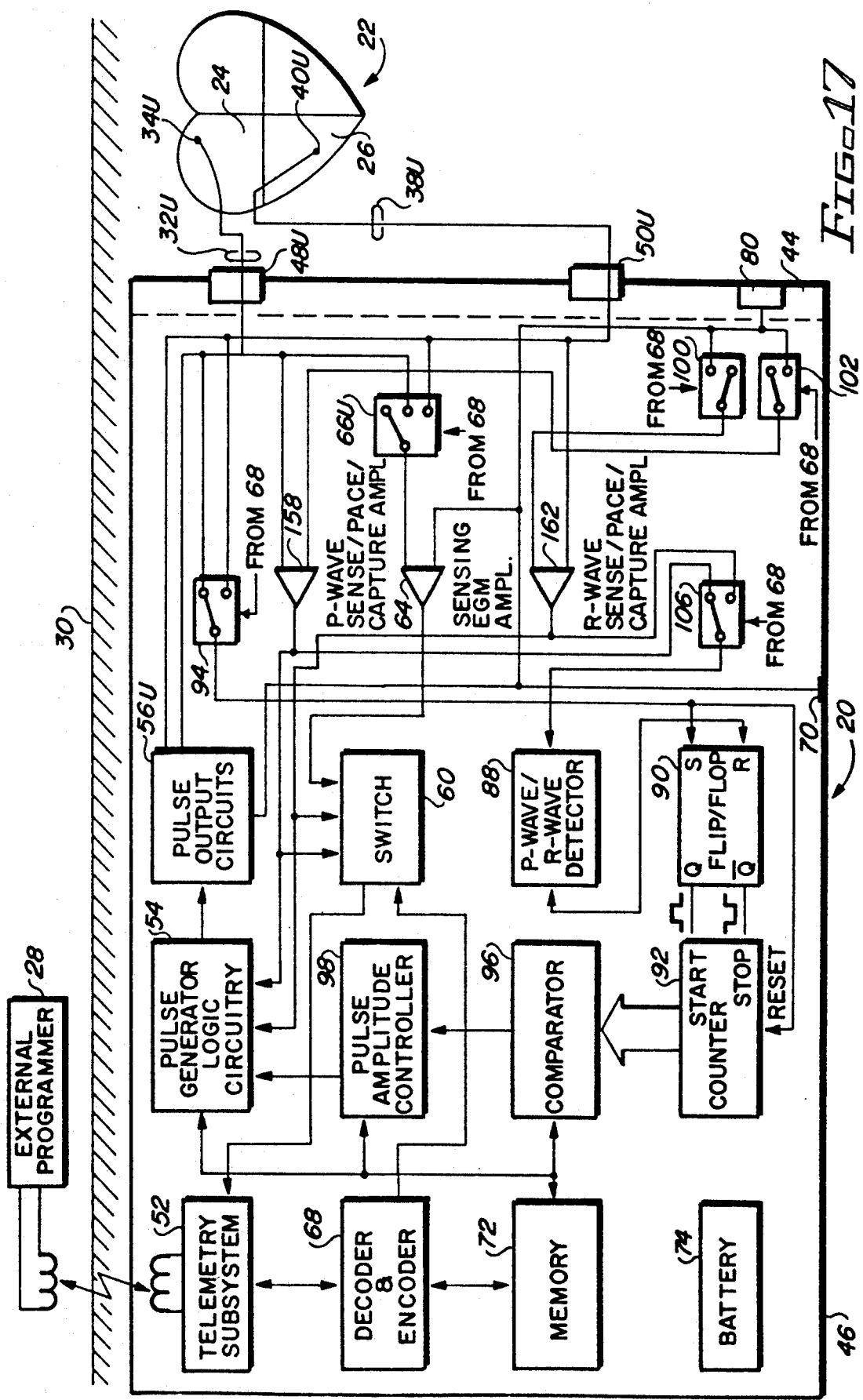

VERIFICATION OF CAPTURE USING AN INDIFFERENT ELECTRODE MOUNTED ON THE PACEMAKER CONNECTOR TOP

BACKGROUND OF THE INVENTION

Field of the Invention

The present invention is directed generally to implantable heart pacemaking systems, and more specifically to a heart pacing system having an improved capability to sense cardiac response, with the system being able to verify capture even when pacing in a bipolar configuration.

"Capture" is defined as a cardiac response which is initiated by a pacemaker stimulation pulse. When a pacemaker stimulation pulse stimulates either the atrium or the ventricle of the heart during an appropriate portion of a cardiac cycle, it is desirable that the stimulation pulse be sufficient to cause the heart to respond to the stimulation pulse provided. Every patient has a threshold which is generally defined as the minimum amount of stimulation energy required to effect capture. It is usually desired to achieve capture at or near the lowest possible energy setting to conserve battery power, thereby extending the useful life of the pacemaker. Typically, once the lowest setting at which capture is reliably obtained is determined, the pulse amplitude is increased somewhat to provide a safety margin so that if the patient's threshold increases, the output of an implanted pacemaker will still be sufficient to maintain capture.

Capture is typically assessed by means of an electrocardiogram (ECG) measured through ECG electrodes placed on the patient's limbs and/or chest. When a patient is connected to a typical ECG monitor and the pacemaker is providing stimulation pulses, the physician monitors the output to assess whether each pacing pulse, which is seen as a spike, is followed by a cardiac response. Ventricular capture is relatively easy to assess in that each ventricular stimulation pulse which achieves capture produces a very large R-wave.

Determination of atrial capture in response to an atrial stimulation pulse is a more difficult task. Atrial capture in response to an atrial stimulation pulses has been viewed on an electrocardiogram as a P-wave following the atrial stimulation pulse by a constant time interval. One previous device utilized dual sensing electrodes and suggested that the heart action is 15 to 20 milliseconds after the stimulus. (See U.S. Pat. No. 4,365,639, to Glodreyer.)

However, the time delay varies considerably depending on the patient's physiology, administered drugs, electrolyte balance, proximity of the sensing electrode to the stimulating electrode, and other factors. Further, it is almost impossible to guarantee that a P-wave will be of sufficient amplitude to be seen on a standard ECG scan. In order to verify atrial capture in patients with intact cardiac condition, the physician must generally pace atrially and observe ventricular response to the paced atrial rate. However in patients with heart block, the physician may not be able to determine atrial capture because of the lack of conduction from the atrium to the ventricle, thus preventing the ventricle from responding to atrial stimulation pulses. In such cases the physician may have to rely on fluoroscope evaluation of cardiac wall motion in response to the atrial stimulation to ascertain atrial capture.

Another method for determining atrial capture is to transmit the signal appearing on the atrial stimulation electrode to an external viewing device. Some of the newer pacemakers have the capability to transmit intracardiac electrogram (IEGM) signals appearing at either the atrial electrode or the ventricular electrode in real time to an external monitoring device for real-time evaluation by a physician. (See, for example, U.S. Pat. No. 4,232,679, to Schulman.)

However, due to the large magnitude of a stimulation pulse with respect to the P-wave signal, and the closeness in time between the stimulation pulse and the occurrence of the P-wave, the atrial sensing amplifiers of conventional pacemakers tend to saturate in the presence of a stimulation pulse and mask the P-wave. Thus, as a practical matter, utilization of IEGM signals derived from the stimulation electrode is not effective for determining if P-wave capture has occurred.

Pacing systems for verifying capture are disclosed in U.S. Pat. Nos. 4,686,988 and 4,817,605, both to the present inventor. In the systems taught in those patents, as in all known systems for verifying capture, one of the two electrodes used to sense capture must be indifferent. This requirement is due to the fact that the two electrodes which are used for pacing will have a charge which inhibits their ability, as a pair, to detect capture.

The systems taught by these two patents use bipolar leads pacing in a unipolar configuration. Thus, only one of the electrodes on each lead is used to pace, with the case of the pacemaker acting as the other pacing electrode. The second electrode on the lead is utilized as an indifferent electrode together with the pacemaker case to sense capture. Thus, for example, in the systems described in U.S. Pat. Nos. 4,686,988 and 4,817,605, the pacing configuration used a unipolar configuration, tip to case. Capture is detected using the ring electrode and the case. U.S. Pat. Nos. 4,686,988 and 4,817,605 are both hereby incorporated herein by reference.

This technique has two significant disadvantages. The first disadvantage is that even with a bipolar pacemaker and bipolar leads, capture can only be sensed when pacing is undertaken in a unipolar configuration. Thus, bipolar pacing and capture detection cannot take place together. The second disadvantage is that the system of U.S. Pat. Nos. 4,686,988 and 4,817,605 cannot be used with unipolar leads.

It is accordingly the primary objective of the present invention that it provide a system which is capable of reliably sensing capture, and that the system be capable of sensing capture on a continual basis. It is a further objective that the system of the present invention be capable of sensing capture while pacing in a bipolar configuration. It is also an objective of the present invention that it provide a system for reliably sensing capture for use with a unipolar pacing system having unipolar leads.

The improved system of the present invention should be relatively simple to implement, so that it will not require an increase in the size of the pacemaker. In addition, it should simultaneously significantly extend the operating life of the pacer, and constantly maintain capture, thus benefiting the patient in two important ways. Finally, it is an objective that all of the aforesaid advantages and objectives be achieved without incurring any substantial relative disadvantage.

SUMMARY OF THE INVENTION

The disadvantages and limitations of the background art discussed above are overcome by the present invention. In accordance with the principles of the present invention, a cardiac pacing system capable of atrial and/or ventricular stimulation and atrial and/or ventricular sensing further includes a capture verification circuit which utilizes an indifferent electrode. In the preferred embodiment, this indifferent electrode is built into the pacemaker at the plastic connector top. Alternately, an additional lead could be used, or an additional electrode could be provided on a lead, although these techniques are felt to be considerably less advantageous. In a bipolar pacing situation, the case could also be used as the indifferent electrode.

The indifferent electrode is preferably disposed on the front or back of the connector top to provide good contact with body tissue. The invention permits a cardiac pacing system to be used with a unipolar lead or leads, or a bipolar lead or leads, and permits bipolar leads to be used for pacing in a bipolar configuration.

Capture is sensed using the indifferent electrode and one of the electrodes on the lead or leads. Either electrode on the lead or leads can be used, although since the tip electrodes are in better contact with heart tissue, the tip electrodes are preferred. The indifferent electrode on the connector top can be used with both leads in a dual chamber pacing system to detect capture in both chambers of the heart. Thus, to detect atrial capture the tip electrode of the atrial lead would be used together with the indifferent electrode. Similarly, to detect ventricular capture the tip electrode of the ventricular lead would be used together with the indifferent electrode.

The improvement in capture verification disclosed herein can be advantageously incorporated in the pacing systems described in the aforementioned U.S. Pat. Nos. 4,817,605 and 4,686,988, and in virtually any other modern pacing system with the addition of little additional circuitry. In the systems of U.S. Pat. Nos. 4,817,605 and 4,686,988, a P-wave sensing amplifier is used as part of the capture sensing and verification technique.

In accordance with the principles of the present invention in a first embodiment, a further amplifier, a capture sense amplifier, is provided. This capture sense amplifier is connected to the indifferent electrode disposed at the connector top and to the tip electrode of one of the pacing leads to sense capture in that lead's heart chamber (the system may switch between leads to sense capture in both chambers). The logic circuitry for capture verification is connected to the output of the capture sense amplifier, and capture is detected.

This system is thus capable of detecting capture in both the atrium and in the ventricle in a dual chamber system, or of one chamber in a single chamber pacing system. Thus, in a bipolar system, the pacing system may pace in a bipolar configuration between the tip and the ring of the pacing lead(s), and sense capture between the tip (preferably) of the pacing lead(s) and the indifferent electrode. Thus, conventional bipolar leads may be used. In a unipolar system, the system may pace in a unipolar configuration between the tip of the lead(s), and sense capture between the tip of the lead(s) and the indifferent electrode.

A second embodiment of the invention provide for automatic setting of stimulation pulse amplitudes in response to a determination of capture thresholds. In this embodiment, the output of the capture sense amplifier is used to determine if capture has occurred. The pulse amplitude (and/or width) may be varied, and when capture is lost, the system will automatically increment the amplitude (and/or width) of the stimulation pulse to a value which is above the lowest pulse amplitude (and/or width) which had capture. In this way, a safety margin is maintained.

In another variation which is the preferred embodiment of the present invention, instead of using a separate capture sensing amplifier, the P-wave sense/pace amplifier and the R-wave sense/pace amplifier are used to detect capture. Normally, during the portion of the time immediately following a stimulation pulse, these amplifiers are in a refractory period in which they are not used to sense. Accordingly, during this time period they may be used to sense capture by switching one of their inputs to monitor the signal from the indifferent electrode.

This embodiment may be used with either bipolar or unipolar leads. With bipolar leads, the pacing system paces in a bipolar configuration between the tip and the ring of the pacing lead(s), and senses capture between the tip (preferably) of the pacing lead(s) and the indifferent electrode using the sense/pace amplifiers. Again, conventional bipolar leads may be used. In a unipolar system, the system paces in a unipolar configuration between the tip of the lead(s), and senses capture between the tip of the lead(s) and the indifferent electrode using the sense/pace amplifiers.

The automatic pulse amplitude setting technique described above may again be used with these additional, preferred embodiments.

It may therefore be seen that the present invention teaches a system which is capable of reliably sensing capture, and that the system is capable of sensing capture on a continual basis. The system of the present invention is capable of sensing capture while pacing in a bipolar configuration with bipolar leads. It is also capable of reliably sensing capture in a unipolar pacing system having unipolar leads.

It is relatively simple to implement, and thus will not increase the size of the pacemaker. In addition, it will significantly extend the operating life of the pacer while constantly maintaining capture, thus benefiting the patient in two important ways. Finally, all of the aforesaid advantages and objectives are achieved without incurring any substantial relative disadvantage.

DESCRIPTION OF THE DRAWINGS

These and other advantages of the present invention are best understood with reference to the drawings, in which:

FIG. 2 is a back view of a pacemaker constructed in accordance with the principles of the present invention showing a preferred location for an indifferent electrode;

FIG. 3 is a front view of a pacemaker constructed in accordance with the principles of the present invention showing an alternate location for placement of the indifferent electrode;

FIG. 4 shows a strip chart tracing of the capture sense signal of the present invention used with a bipolar lead, together with a strip chart tracing of the surface ECG for reference, at a 7.5 volt pulse amplitude;

FIG. 5 shows a strip chart tracing of the capture sense signal of the present invention used with a bipolar lead, together with a strip chart tracing of the surface ECG for reference, at a 1.5 volt pulse amplitude;

FIG. 6 shows a strip chart tracing of the capture sense signal of the present invention used with a bipolar lead, together with a strip chart tracing of the surface ECG for reference, at a 1.0 volt pulse amplitude;

FIG. 17 is a schematic block diagram of a dual chamber, unipolar cardiac pacing system as shown in FIG. 15, additionally including means for automatically controlling the output pulse characteristics.

DETAILED DESCRIPTION OF THE PREFERRED EMBODIMENT

The following description is based on the operation of a cardiac pacing system operating in a DDD mode, however, it will be understood that the invention is not so limited, and may be used in other types of pacing modes as well. Specifically, the present invention is equally applicable to single or dual chamber pacing, to unipolar or bipolar leads, pacemakers, and pacing configurations, and to rate-responsive or non-rate-responsive pacing systems. The system of the present invention in the preferred embodiments is entirely contained within the pacemaker, and as such may be used with any pacemaker leads.

Figure 1:
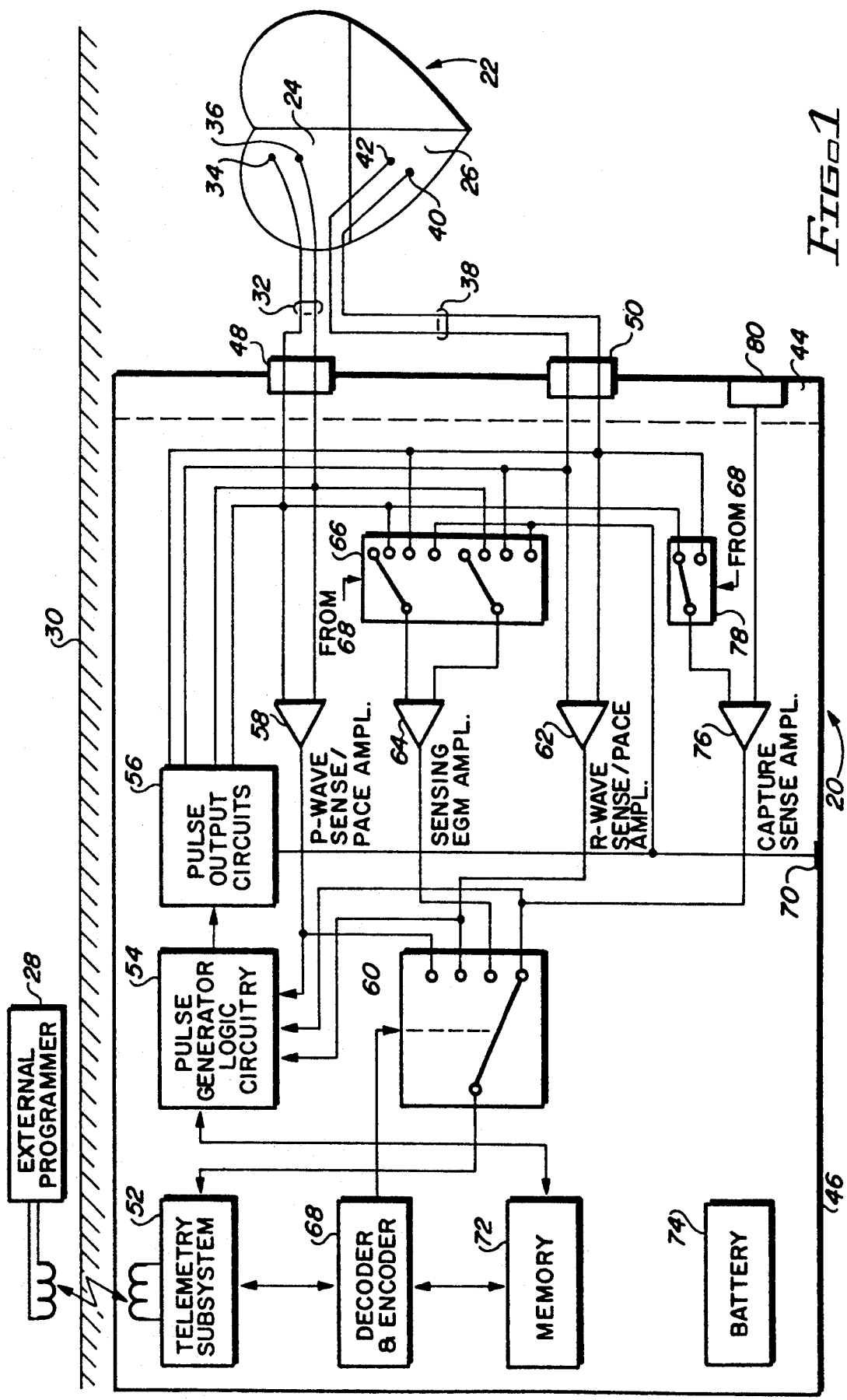
FIG. 1 is a schematic block diagram of a dual chamber, bipolar cardiac pacing system constructed in accordance with the principles of the present invention.

A schematic block diagram of an implanted pacing system 20 constructed in accordance with the principles of the present invention is shown in FIG. 1. The pacing system 20 is connected to a patient's heart 22 having a right atrium 24 and a right ventricle 26. The pacing system 20 is capable of electromagnetically communicating with an external programmer 28 located external to the skin 30 of the patient. The programmer 20 includes a telemetry transmitter and receiver and a monitor, as is well known in the art.

A conventional bipolar atrial lead 32 is provided having a first or tip electrode 34 at its distal end, and a second or ring electrode 36 spaced from the tip electrode 34. The tip electrode 34 is located in contact with atrial tissue in the right atrium 24.

A conventional bipolar ventricular lead 38 is located in the right ventricle 26, and has a tip electrode 40 and a ring electrode 42, also in typical bipolar configuration. The tip electrode 40 is located in contact with ventricular tissue in the right ventricle 26.

The pacing system 20 also includes an implantable housing containing the various electrical components. The housing consists of a top portion referred to as the connector top 44, consisting principally of plastic or another type of synthetic, nonconductive material, and a lower metal case or pacemaker can 46, typically made of titanium. The bipolar atrial lead 32 and the bipolar ventricular lead 38 are electrically and mechanically connected to the housing via respective conventional bipolar lead connectors 48 and 50 located in the connector top 44.

The pacing system 20 further includes a telemetry subsystem 52 for transmitting data and parameter values to the external telemetry transmitter and receiver located in the programmer 28, and for receiving data instructions and the like from the programmer 28.

The pacing system 20 also includes pulse generator logic circuitry 54 which controls pulse output circuits 56 for providing both atrial and ventricular stimulation pulses. The bipolar atrial output from the pulse output circuits 56 is connected through the atrial lead connector 48 to the tip electrode 34 and the ring electrode 36 of the bipolar atrial lead 32 for stimulation of the atrium. Similarly, the bipolar ventricular output from the pulse output circuits 56 is connected through the ventricular lead connector 50 to the tip electrode 40 and the ring electrode 42 of the bipolar ventricular lead 38 for stimulation of the ventricle.

A P-wave sense/pace amplifier 58 is connected to the bipolar atrial output of the pulse output circuits 56, and, via the atrial lead connector 48, to the tip electrode 34 and the ring electrode 36 of the bipolar atrial lead 32 for receiving electrical signals there present. The output of the P-wave sense/pace amplifier 58 is connected to the pulse generator logic circuitry 54, and to a switch 60, the purpose of which will be explained below. The implanted pacemaker, if operating as a "demand" type pacer, will not provide stimulation to the atrium when the output of the P-wave sense/pace amplifier 58 indicates the presence of an intrinsic or spontaneous P-wave. The P-wave sense/pace amplifier 58 has sufficiently broad bandpass characteristics (typically 10–100 Hz) so that electrical signals of substantially all intrinsic atrial activity will be sensed.

An R-wave sense/pace amplifier 62 is also provided, and is connected to the bipolar ventricular output of the pulse output circuits 56, and, via the ventricular lead connector 50, to the tip electrode 40 and the ring electrode 42 of the bipolar ventricular lead 38 for receiving electrical signals there present. The output of the R-wave sense/pace amplifier 62 is connected to the pulse generator logic circuitry 54, and to the switch 60. Again, the implanted pacemaker, if operating as a "demand" type pacer, will not provide stimulation to the ventricle when the output of the R-wave sense/pace amplifier 62 indicates the presence of an intrinsic or spontaneous R-wave. The R-wave sense/pace amplifier 62 has sufficiently broad bandpass characteristics (typically 10-100 Hz) so that electrical signals of substantially all intrinsic ventricular activity will be sensed.

An EGM sensing amplifier 64 has each of its inputs connected to one side of one switch contained in a double switch 66, which is telemetrically operated by a decoder and encoder 68, which is operatively connected to the telemetry subsystem 52. Depending upon the state of the switch 66, one input to the EGM sensing amplifier 64 will be connected either to the tip electrode 34 (of the bipolar atrial lead 32), to the tip electrode 40 (of the bipolar ventricular lead 38), or to a direct electrical connection 70 to the pacemaker can 46. The other input to the EGM sensing amplifier 64 will be connected either to the ring electrode 36 (of the bipolar atrial lead 32), to the ring electrode 42 (of the bipolar ventricular lead 38), or to the direct electrical connection 70 to the pacemaker can 46. The output of the EGM sensing amplifier 64 is also connected to the switch 60.

The output of the switch 60 is connected to the telemetry subsystem 52 so that the output of any one of the amplifiers 58, 62, or 64 (or an additional amplifier which will be discussed below) can be transmitted in real time to the programmer 28, where the output can be visually displayed on a monitor and permanently recorded as a tracing on a strip recorder. The specific amplifier output to be externally transmitted may be selected by a physician via instructions transmitted by the programmer 28 and received by the implanted telemetry subsystem 52.

These instructions are decoded by the decoder and encoder 68, which, as noted earlier, controls the operation of the switches 60 and 66 (as well as an additional switch to be discussed below). The output of the decoder and encoder 22 sets the position of the switch 60 to determine which amplifier output will be externally transmitted. It is also possible to externally transmit more than one amplifier output at a time by use of a multiplexing system (not shown).

The EGM sensing amplifier 64 is used by the physician for a single purpose. That purpose is as a diagnostic tool to evaluate lead integrity and placement. The EGM sensing amplifier 64 allows the physician to, in effect, connect an ECG machine directly to the leads 32 and 38, without requiring surgery to be performed on the patient. Typically, the EGM sensing amplifier 64 is used only after initial placement of the leads 32 and 38, or if there is a problem associated with lead placement or integrity. If the output of the EGM sensing amplifier 64 is to be telemetered out, the switch 60 will select the EGM sensing amplifier 64, and the switch 66 will select which electrical path associated with the leads 32 and 38 is to be tested.

A memory 72 is also provided, which receives parameter information from the decoder and encoder 68, with this information being used primarily to control the pulse generator logic circuitry 54. A battery 74 is also schematically indicated as being present within the pacemaker can 46, with the electrical connections to the various components being omitted for clarity. Such connections are easily ascertainable by those skilled in the art.

The components described up to this point are shown in the art for the most part, particularly in the above-incorporated by reference U.S. Pat. Nos. 4,686,988 and 4,817,605. The additional components described below operate together with the components described above to achieve the objectives of the present invention.

The pacing system 20 includes a capture sense amplifier 76 having two inputs. The first input to the capture sense amplifier 76 is connected to a switch 78, which selectively connects the capture sense amplifier 76 (via the connectors 32 and 38) to either the tip electrode 34 (of the bipolar atrial lead 32) or the tip electrode 40 (of the bipolar ventricular lead 38). The switch is operated by the decoder and encoder 68 described above to select whether atrial or ventricular capture is to be determined. The other input to the capture sense amplifier 76 is connected to an indifferent electrode 80 located in the connector top 44 and exposed to the body. The indifferent electrode 80 is thus an electrode mounted in the connector top 44, and electrically separate from all the other electrodes used for pacing and sensing.

A preferred location for the indifferent electrode 80 is shown in FIG. 2. FIG. 2 shows what is conventionally referred to as the back of a pacemaker (the side which faces the interior of the patient's chest), and as can be seen the indifferent electrode 80 is shown as a button electrode located in the connector top 44. The indifferent electrode 80 may, however, also be located on what is conventionally referred to as the front of the pacemaker (the side which faces the patient's skin), as shown in FIG. 3. Alternately, the indifferent electrode 80 could be a short additional lead (not shown) extending from the connector top 44. The indifferent electrode 80 could also be an additional electrode located on a pacing lead, although this is not viewed as being as advantageous as the preferred embodiment.

Referring again to FIG. 1, the output of the capture sense amplifier 76 is supplied to the switch 60, as well as to the pulse generator logic circuitry 54. The indifferent electrode 80 is used as one of two electrodes for sensing signals to verify capture. In previously known systems wherein capture verification was desired, the electrical path for sensing capture existed between one of the lead electrodes, such as the ring electrode, and the case. The electrical path for pacing, as well as for pacing-related sensing, was between the other lead electrode and the case. This meant that even using a bipolar lead, only unipolar pacing could be undertaken, because the other electrode of the lead was occupied for the purpose of capture verification.

In sharp contrast, in the system shown in FIG. 1, the electrical path for pacing, as well as for pacing-related sensing, is bipolar, and is between the tip electrode 34 and the ring electrode 36 (both of the bipolar atrial lead 32) for stimulating the atrium 24, and between the tip electrode 40 and the ring electrode 42 (both of the bipolar ventricular lead 38) for stimulating the ventricle 26. Capture may be sensed between either electrode of either lead and the indifferent electrode 80 located in the connector top 44.

Additionally, it has been found that the capture sense signal obtained via the electrode 80 is much better suited for accurate capture verification than the ring electrode-to-case signal which was used in previously known systems. The use of the indifferent electrode 80 located in the connector top 44 thus not only provides the advantage of not precluding various pacing options, but also provides the advantage of improved reliability in capture verification.

For reasons explained in detail in the above-incorporated by reference U.S. Pat. Nos. 4,817,605 and 4,686,988, sensing a signal for verification of capture is extremely difficult because of the saturation voltage present following the generation of an stimulation pulse. It is therefore particularly difficult to accurately detect the voltage representing P-waves (which are smaller than R-waves) while discriminating against other signals present in the atrium.

As shown in FIGS. 4 through 6, however, the use of the indifferent electrode 80 located at the connector top 44 provides extremely clear signals for use in atrial capture verification. FIGS. 4 through 6 show strip chart tracings showing the efficacy of the indifferent electrode 80 in atrial capture verification. In each of FIGS. 4 through 9, the telemetered output of the capture sense amplifier 76 is shown as the top trace, and the surface ECG is shown as the bottom trace.

FIGS. 4 through 6 were obtained using a bipolar lead configuration. In all of these figures except FIG. 6, the surface ECG gain was 1.0 millivolt per division, the intracardiac EGM gain was 20 millivolts per division and the chart speed was 50 millimeters per second. For FIG. 6, the surface ECG gain was 1.0 millivolts per division, the intracardiac EGM gain was 10 millivolts per division and the chart speed was 50 millimeters per second.

In FIG. 4, the spike 82 in the ECG signal is a pacing stimulation pulse having an amplitude of 7.5 volts. Capture is indicated at the output of the amplifier 76 beginning at 84, which can be seen to be slightly in advance of the detection of the same cardiac activity sequence in the ECG signal beginning at 86.

In the example of FIG. 5, the pacing stimulation pulse amplitude has ben reduced to 1.5 volts, and it is thus not visible on the ECG trace. Nonetheless, it can still be seen in FIG. 5 that capture has occurred, again such verification being seen at 84 in the output of the amplifier 76 slightly in advance of the recording of the same event beginning at 86 in the ECG trace.

In FIG. 6, the scale for the ECG trace has been enlarged so that the pacing spikes 82, now at 1.0 volts, can again be seen. It can also be seen that no evoked response has occurred, and thus there is loss of capture.

Figure 7:
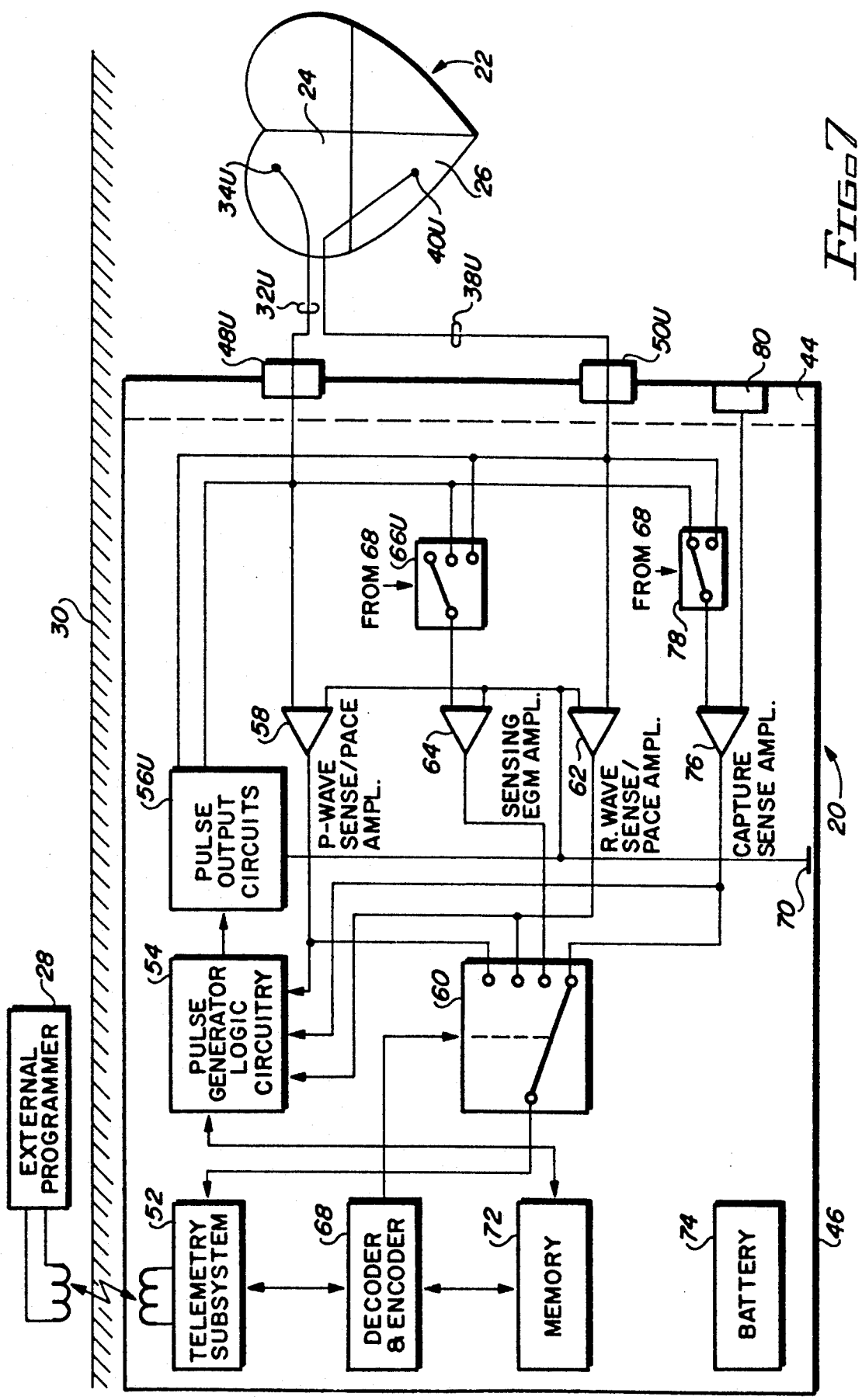
FIG. 7 is a schematic block diagram of a dual chamber, unipolar cardiac pacing system constructed in accordance with the principles of the present invention.

Referring next to FIG. 7, a unipolar dual chamber pacing configuration using the principles of the present invention is illustrated. Except as noted below, the components and functions of FIG. 7 are identical to those in FIG. 1, and similar reference numerals have been used. Note that the letter U has been added to those components which differ in the unipolar embodiment.

A conventional unipolar atrial lead 32U is provided having a first or tip electrode 34U at its distal end. The tip electrode 34U is located in contact with atrial tissue in the right atrium 24. A conventional unipolar ventricular lead 38U is located in the right ventricle 26, and has a tip electrode 40U. The tip electrode 40U is located in contact with ventricular tissue in the right ventricle 26. The unipolar atrial lead 32U and the unipolar ventricular lead 38U are electrically and mechanically connected to the housing via respective conventional unipolar lead connectors 48 and 50 located in the connector top 44.

The pulse output circuits 56U provide both atrial and ventricular stimulation pulses, this time through the unipolar leads 32U and 38U and the direct electrical connection 70 to the pacemaker can 46. The unipolar atrial output from the pulse output circuits 56U is connected through the atrial lead connector 48U to the tip electrode 34U of the unipolar atrial lead 32U (and the direct electrical connection 70 to the pacemaker can 46) for stimulation of the atrium. Similarly, the unipolar ventricular output from the pulse output circuits 56U is connected through the ventricular lead connector 50U to the tip electrode 40U of the unipolar ventricular lead 38U (and the direct electrical connection 70 to the pacemaker can 46) for stimulation of the ventricle.

One side of the P-wave sense/pace amplifier 58 is connected to the unipolar atrial output of the pulse output circuits 56U, and, via the atrial lead connector 48U, to the tip electrode 34U of the unipolar atrial lead 32U. The other side of the P-wave sense/pace amplifier 58 is connected to the direct electrical connection 70 to the pacemaker can 46.

One side of the R-wave sense/pace amplifier 62 is connected to the unipolar ventricular output of the pulse output circuits 56U, and, via the ventricular lead connector 50U, to the tip electrode 40U of the unipolar ventricular lead 38U. The other side of the R-wave sense/pace amplifier 62 is connected to the direct electrical connection 70 to the pacemaker can 46.

The EGM sensing amplifier 64 has one of its inputs connected to one side of a switch 66U. Depending upon the state of the switch 66U, one input to the EGM sensing amplifier 64 will be connected either to the tip electrode 34U (of the unipolar atrial lead 32U), or to the tip electrode 40U (of the unipolar ventricular lead 38U). The other input to the EGM sensing amplifier 64 is connected to a direct electrical connection 70 to the pacemaker can 46.

In the system shown in FIG. 7, the electrical path for pacing, as well as for pacing-related sensing, is unipolar, and is between the tip electrode 34U (of the unipolar atrial lead 32U) and the direct electrical connection 70 to the pacemaker can 46 for stimulating the atrium 24, and between the tip electrode 40U (of the unipolar ventricular lead 38U) and the direct electrical connection 70 to the pacemaker can 46 for stimulating the ventricle 26. Capture may be sensed between the tip electrode of either lead and the indifferent electrode 80 located in the connector top 44.

Figure 8:
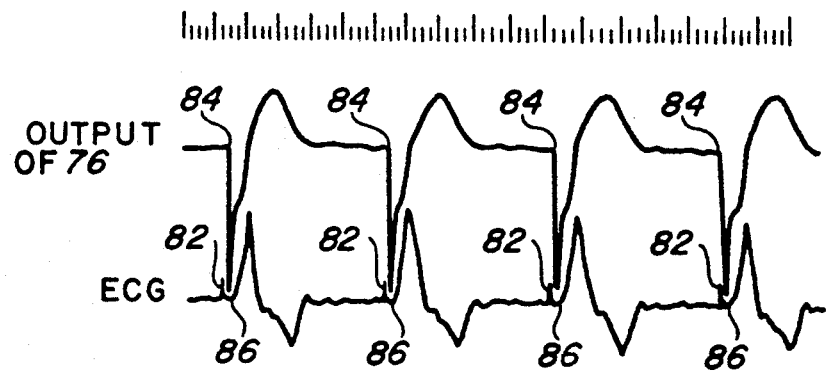
FIG. 8 shows a strip chart tracing of the capture sense signal of the present invention used with a unipolar lead, together with a strip chart tracing of the surface ECG for reference, at a 7.5 volt pulse amplitude.
Figure 9:
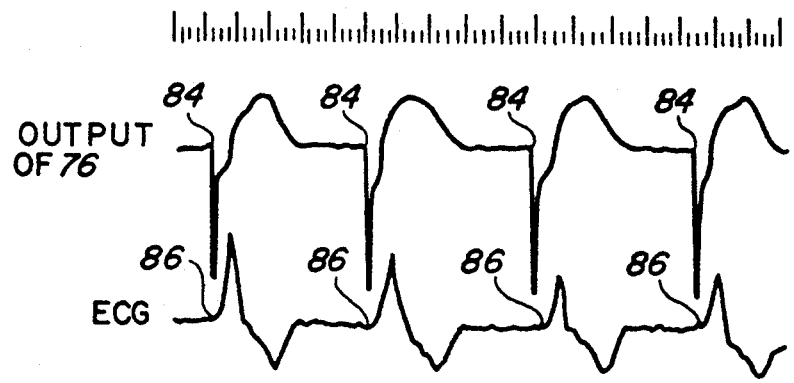
FIG. 9 shows a strip chart tracing of the capture sense signal of the present invention used with a unipolar lead, together with a strip chart tracing of the surface ECG for reference, at a 1.5 volt pulse amplitude.
Figure 10:
FIG. 10 shows a strip chart tracing of the capture sense signal of the present invention used with a unipolar lead, together with a strip chart tracing of the surface ECG for reference, at a 1.0 volt pulse amplitude.

FIGS. 8 through 10 show strip chart tracings showing the efficacy of the indifferent electrode 80 in atrial capture verification using a unipolar lead configuration. Again in each of FIGS. 8 through 10, the telemetered output of the capture sense amplifier 76 is shown as the top trace, and the surface ECG is shown as the bottom trace. In all of these figures, the surface ECG gain was 1.0 millivolt per division, the intracardiac EGM gain was 20 millivolts per division and the chart speed was 50 millimeters per second.

In FIG. 8, the pacing spike 82 at 7.5 volts can again be seen, and again the output of the amplifier beginning at 84 shows that capture has occurred. In FIG. 9, the pacing pulse amplitude has again been reduced to 1.5 volts, and thus it is not visible in the ECG trace, however, it can be seen that capture has still occurred. In FIG. 10, the amplitude of the pacing pulse has been reduced to 1.0 volts, and again there is loss of capture.

Figure 11:
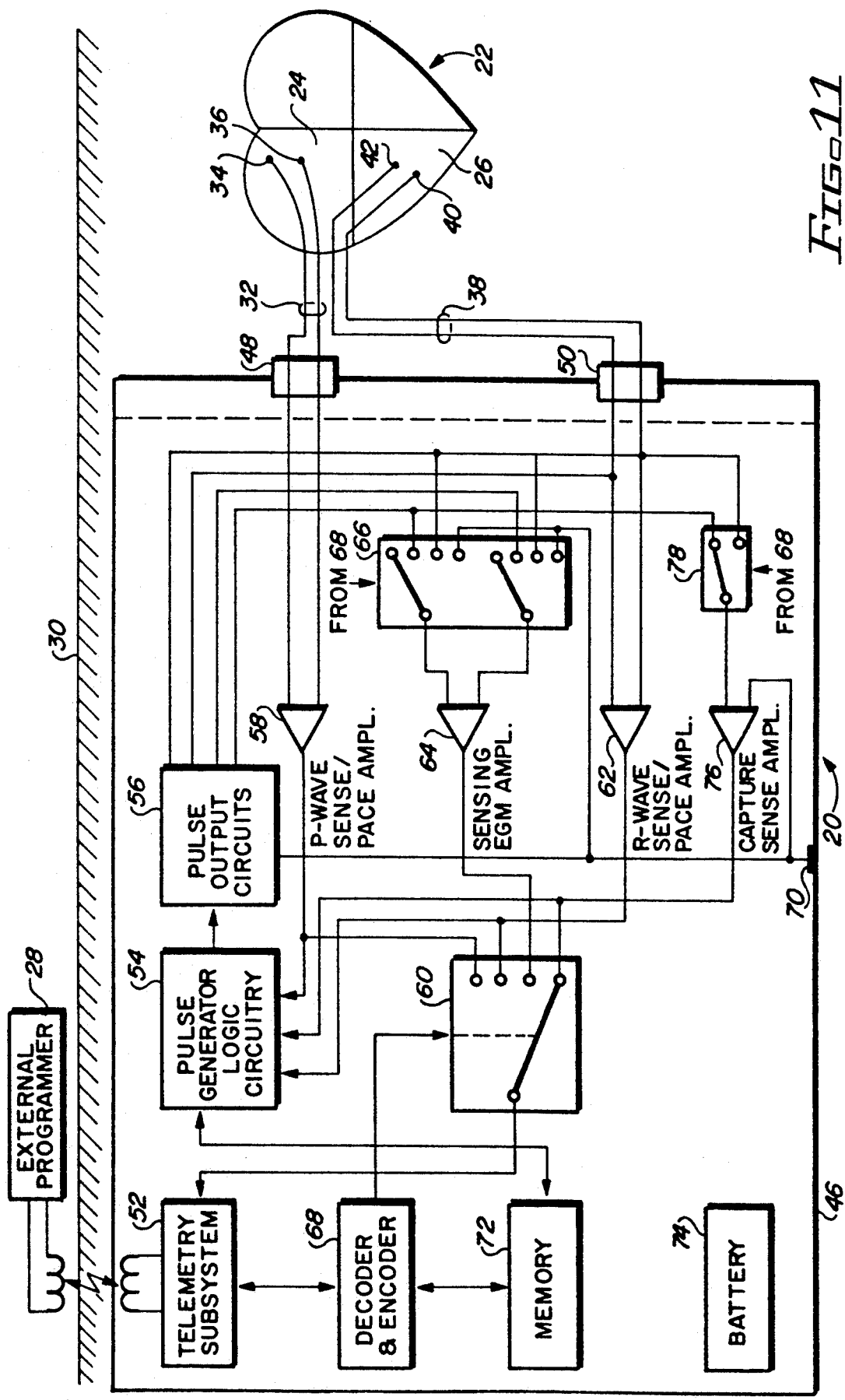
FIG. 11 is a schematic block diagram of a dual chamber, bipolar cardiac pacing system similar to the one shown in FIG. 1, but using the pacemaker case as the indifferent electrode.

As mentioned above, in a bipolar pacing situation it is possible to use the pacemaker can as the indifferent electrode. Such an embodiment is illustrated in FIG. 11, wherein the input to the capture sense amplifier 76 connected to the indifferent electrode 80 in FIG. 1 is connected to the direct electrical connection 70 to the pacemaker can 46 in FIG. 11. The components and functions of FIG. 11 are identical to those in FIG. 1, and similar reference numerals have been used. Note that this is only possible in a bipolar pacing configuration in which the can is used neither for pacing nor for sensing (other than for capture). As such, this embodiment is not preferred since it limits the configuration of a pacemaker to a bipolar pacing and sensing configuration.

Figure 12:
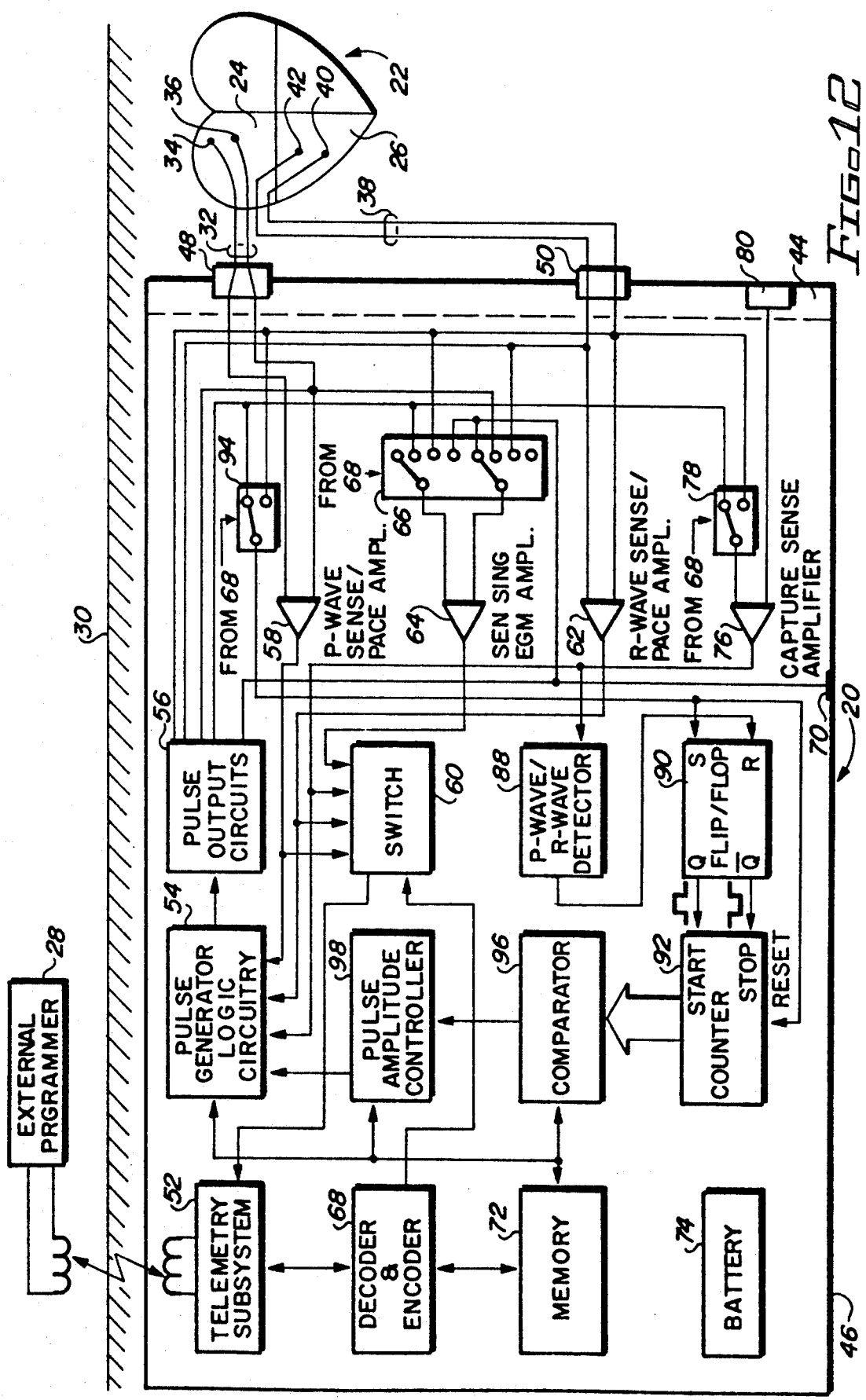
FIG. 12 is a schematic block diagram of a dual chamber, bipolar cardiac pacing system as shown in FIG. 1, additionally including means for automatically controlling the output pulse characteristics.

A further embodiment of the invention is shown in FIG. 12. This embodiment incorporates into the bipolar embodiment of FIG. 1 means for automatically controlling the characteristics of the atrial and ventricular output stimulation pulses to select pulse amplitudes (and/or pulse widths) which will maintain capture without using an unnecessarily large amplitude (and/or width). This minimizes the rate of battery current drain, thereby preventing premature battery depletion.

The embodiment of FIG. 12 is identical to that of FIG. 1 except for the addition of circuitry to control the automatic selection of pulse amplitude (and/or pulse width). Most of the components and functions of FIG. 7 are identical to those in FIG. 1, and similar reference numerals have been used. The switch 60, which is not shown in detail in FIG. 12, is nevertheless identical to the switch 60 of FIG. 1.

In the embodiment of FIG. 10, the output of the capture sense amplifier 76 is additionally connected to a P-wave/R-wave detector 88, which includes conventional circuitry for producing a pulse output whenever the P-wave signal or R-wave signal (whichever is being detected at that point in time) exceeds a predetermined level for a predetermined time. The P-wave/R-wave detector 88 has input bandpass characteristics similar to that of the P-wave sense/pace amplifier 58 and the R-wave sense/pace amplifier 62 to attenuate other electrical signals in the atrium as explained above.

The output of the P-wave detector 88 is supplied to a reset terminal of a monostable flip-flop 90. A counter 92 is provided which has its start input connected to the Q output of the flip-flop 90, and its stop input connected to the Q-BAR output of the flip-flop 90. The set input of the flip-flop 90 and the reset input of the counter 92 are connected to one side of a switch 94. The switch 94 selectively connects to either the atrial stimulation pulse supplied from the pulse output circuits 56 to the tip electrode 34 (of the bipolar atrial lead 32), or the ventricular stimulation pulse supplied from the pulse output circuits 56 to the tip electrode 40 (of the bipolar ventricular lead 38). Thus, when there is a pacing pulse, the counter 92 will be reset and the flip-flop 90 will start the counter.

When the P-wave/R-wave detector 88 detects an evoked response, an output signal will be supplied to reset the flip-flop 90, which will stop the counter. If no evoked response occurs within a particular, relatively uniform period of time in which is should have occurred if capture was present, then there is no capture. Accordingly, if the output of the counter 92 is above a certain level, and/or if it is not consistent, capture has occurred. If it is below that level, and/or if it is relatively consistent, then capture has occurred.

The output of the counter 92 is connected to the input of a comparator 96, having an output connected to a pulse amplitude (and/or pulse width) controller 98. The comparator 96 and the pulse amplitude (and/or pulse width) controller 37 are further controlled by signals from the memory 72. The comparator 96 may be of any standard type known in the art, either digital or analog, which compares the level of the counter 92 (determined by the elapsed time between the start and stop inputs to the counter 92) for determining time coincidence.

If the elapsed times between the start and stop pulse inputs to the counter 92 are below a certain period, and/or relatively stable for successive stimulation pulse/evoked response intervals, the pulse amplitude (and/or pulse width) controller 98 may be operated to reduce the output voltage of the stimulation pulses through the pulse generator logic circuitry 54, until such time as the output of the comparator 96 indicates that the elapsed time intervals between start and stop inputs to the counter 92 are too long and/or not equal. At that point, the pulse amplitude (and/or pulse width) controller 98 increases the pulse amplitude and/or pulse width of the stimulation pulses until the counts provided by the counter 92 are below the preset value and/or relatively consistent.

The pacemaker through its memory 72 thus can be programmed to effect this resetting of stimulation pulse amplitude (and/or pulse width) automatically at predetermined time intervals, such as every month, without requiring the presence of an attending physician.

Figure 13:
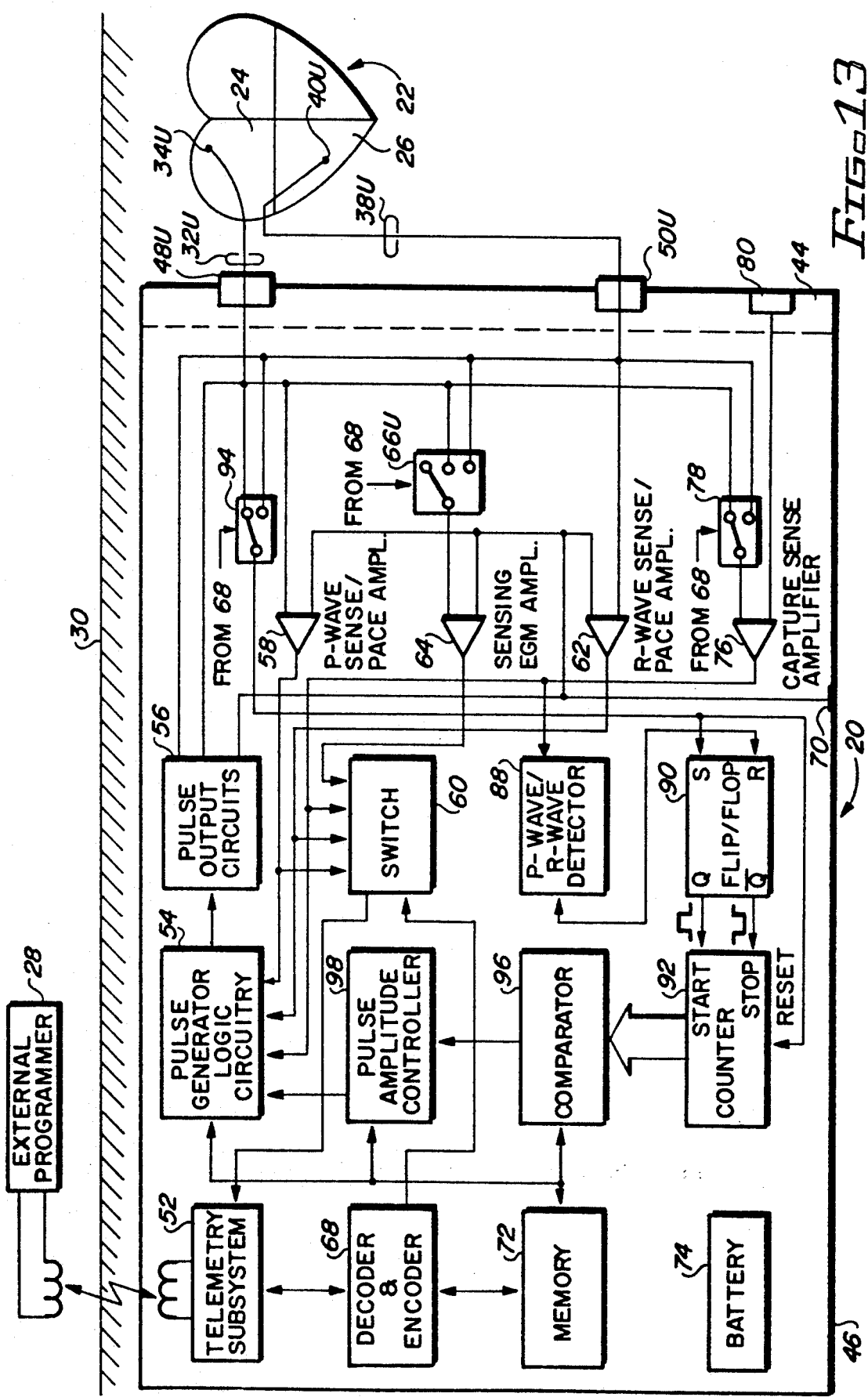
FIG. 13 is a schematic block diagram of a dual chamber, unipolar cardiac pacing system as shown in FIG. 7, additionally including means for automatically controlling the output pulse characteristics.

Referring next to FIG. 13, the adjustment system for varying pulse amplitude (and/or pulse width) of FIG. 12 is illustrated in a unipolar embodiment similar to FIG. 7. The components and functions of FIG. 13 are identical to those in FIGS. 7 and 12, and similar reference numerals have been used. No further discussion of FIG. 13 is therefore believed to be necessary.

The embodiments of the present invention discussed above are the simplest to understand, with a separate capture sense amplifier 76. They are, however, not the simplest ways to implement the principles of the present invention. In fact, it is not necessary to add an additional amplifier to the systems of a pacemaker not having the present invention incorporated therein. It is possible to use the P-wave sense/pace amplifier and the R-wave sense/pace amplifier contained in a standard pacing circuit to perform the functions of the capture sensing amplifier 76 of FIGS. 1, 7, and 11 through 13.

In order to understand how this is possible, it is necessary to first understand how the P-wave sense/pace amplifier and the R-wave sense/pace amplifier in a pacemaker are used. Following the delivery of a pacing spike to the atrium, there is a refractory period in which the P-wave sense/pace amplifier will not sense cardiac activity. This refractory period is divided into two segments: an absolute refractory period, which is followed by a relative refractory period.

During the absolute refractory period, which is typically 100 milliseconds, the P-wave sense/pace amplifier is effectively out of the circuit and cannot sense anything. Following the absolute refractory period during the relative refractory period, the P-wave sense/pace amplifier is used to sense during a period in which no signal should be sensed. This period is used to check for noise.

Similarly, following the delivery of a pacing spike to the ventricle, there is a refractory period in which the R-wave sense/pace amplifier will not sense cardiac activity. This refractory period is also divided into an absolute refractory period followed by a relative refractory period.

During the absolute refractory period, which is also typically 100 milliseconds, the R-wave sense/pace amplifier is also effectively out of the circuit and cannot sense anything. Following the absolute refractory period during the relative refractory period, the R-wave sense/pace amplifier is used to sense during a period in which no signal should be sensed. This period is also used to check for noise.

Thus, there is a period of time for both the P-wave sense/pace amplifier and the R-wave sense/pace amplifier in which they are not used. It has been determined that this period of time is precisely the period of time in which capture is sensed by the capture sense amplifier 76. Thus, it is possible to switch the P-wave sense/pace amplifier and the R-wave sense/pace amplifier to perform the capture sensing during the absolute refractory periods. This scheme is shown in FIGS. 14 through 17.

Figure 14:
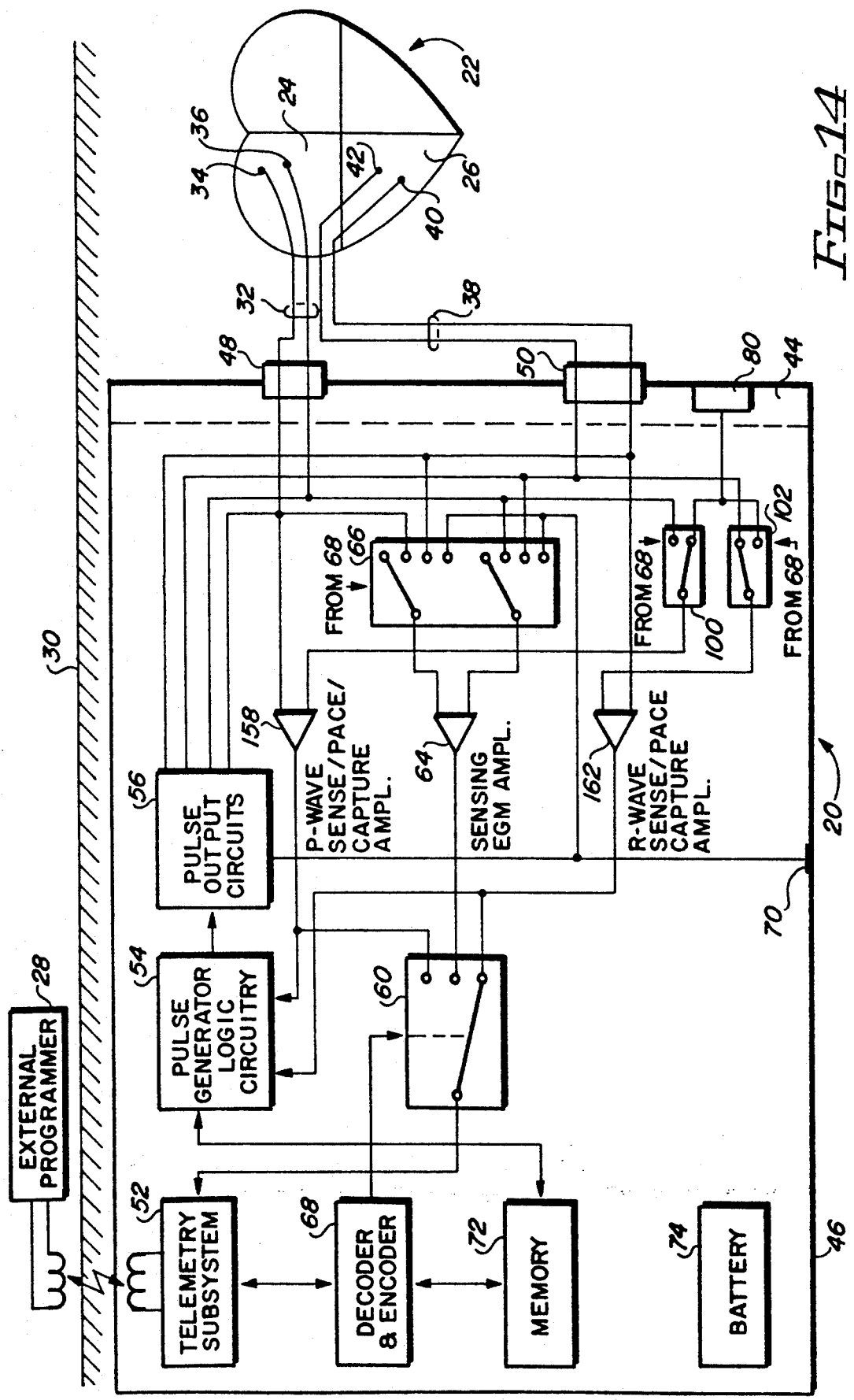
FIG. 14 is a schematic block diagram of a dual chamber, bipolar cardiac pacing system similar to the system shown in FIG. 1, but using the sense/pace amplifiers to additionally detect capture.

FIG. 14 is a bipolar system similar to FIG. 1 which, except as noted below, is identical in components and functions of to those in FIG. 1, with similar reference numerals being used. The main difference of FIG. 14 is that the capture sense amplifier 76 is not used. Instead, a P-wave sense/pace/capture amplifier 158 and an R-wave sense/pace/capture amplifier 162 are used in place of the P-wave sense/pace amplifier 58 and the R-wave sense/pace amplifier 62, respectively. In addition, the inputs to the P-wave sense/pace/capture amplifier 158 and the R-wave sense/pace/capture amplifier 162 are somewhat different.

One of the inputs to the P-wave sense/pace/capture amplifier 158 is connected to the side of the bipolar atrial output of the pulse output circuits 56 which, via the atrial lead connector 48, is connected to the tip electrode 34 of the bipolar atrial lead 32. The other input to the P-wave sense/pace/capture amplifier 158 is connected to a switch 100 which selects either the side of the bipolar atrial output of the pulse output circuits 56 which, via the atrial lead connector 48, is connected to the ring electrode 36 of the bipolar atrial lead 32, or the indifferent electrode 80.

When the switch 100 connects the other input of the P-wave sense/pace/capture amplifier 158 to the side of the bipolar atrial output of the pulse output circuits 56 which, via the atrial lead connector 48, is connected to the ring electrode 36 of the bipolar atrial lead 32, the P-wave sense/pace/capture amplifier 158 acts as an atrial sense/pace amplifier. When the switch 100 connects the other input of the P-wave sense/pace/capture amplifier 158 to the indifferent electrode 80, the P-wave sense/pace/capture amplifier 158 acts as an atrial capture amplifier. The switch 100 is operated by a signal from the decoder and encoder 68.

Similarly, one of the inputs to the R-wave sense/pace/capture amplifier 162 is connected to the side of the bipolar ventricular output of the pulse output circuits 56 which, via the ventricular lead connector 50, is connected to the tip electrode 40 of the bipolar ventricular lead 38. The other input to the R-wave sense/pace/capture amplifier 162 is connected to a switch 102 which selects either the side of the bipolar ventricular output of the pulse output circuits 56 which, via the ventricular lead connector 50, is connected to the ring electrode 42 of the bipolar ventricular lead 38, or the indifferent electrode 80.

When the switch 102 connects the other input of the R-wave sense/pace/capture amplifier 162 to the side of the bipolar ventricular output of the pulse output circuits 56 which, via the ventricular lead connector 50, is connected to the ring electrode 42 of the bipolar ventricular lead 38, the R-wave sense/pace/capture amplifier 162 acts as a ventricular sense/pace amplifier. When the switch 102 connects the other input of the R-wave sense/pace/capture amplifier 162 to the indifferent electrode 80, the R-wave sense/pace/capture amplifier 162 acts as a ventricular capture amplifier. The switch 102 is operated by a signal from the decoder and encoder 68.

The operation of the system of FIG. 14 may now be discussed. Following delivery of an atrial pacing pulse, the P-wave sense/pace/capture amplifier 158 will sense atrial capture during the absolute refractory period (approximately 100 milliseconds) which follows the atrial pacing pulse. Similarly, following delivery of a ventricular pacing pulse, the R-wave sense/pace/capture amplifier 162 will sense ventricular capture during the absolute refractory period (approximately 100 milliseconds) which follows the ventricular pacing pulse. In sensing capture, the system of FIG. 14 operates in a manner similar to the system of FIG. 1.

Figure 15:
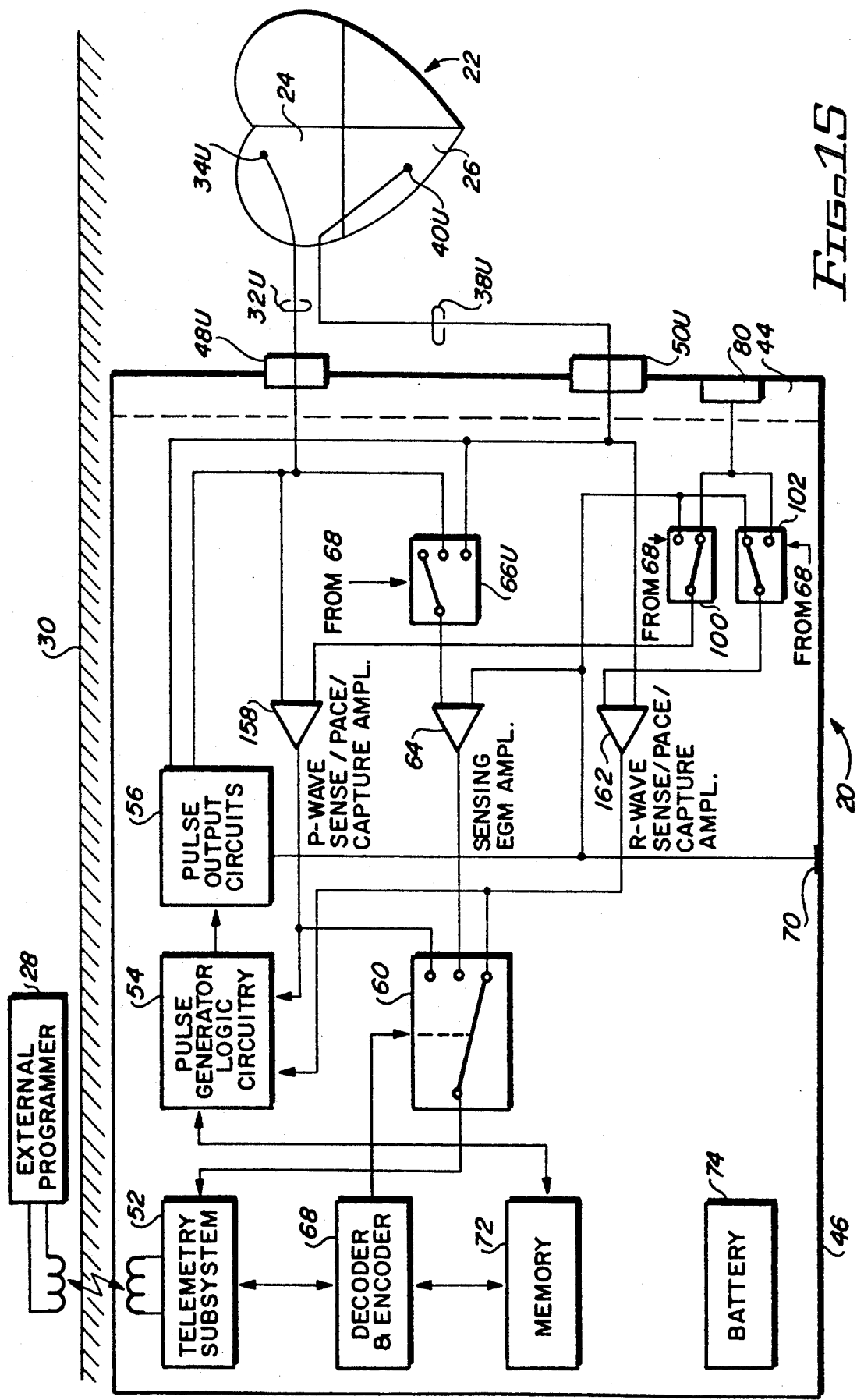
FIG. 15 is a schematic block diagram of a dual chamber, unipolar cardiac pacing system similar to the system shown in FIG. 7, but using the sense/pace amplifiers to additionally detect capture.

FIG. 15 is a unipolar system similar to FIG. 7 which, except as noted below, is identical in components and functions of to those in FIG. 7, with similar reference numerals being used. The main difference of FIG. 15 is that the capture sense amplifier 76 is not used. Instead, a P-wave sense/pace/capture amplifier 158 and an R-wave sense/pace/capture amplifier 162 are used in place of the P-wave sense/pace amplifier 58 and the R-wave sense/pace amplifier 62, respectively. In addition, the inputs to the P-wave sense/pace/capture amplifier 158 and the R-wave sense/pace/capture amplifier 162 are somewhat different.

One of the inputs to the P-wave sense/pace/capture amplifier 158 is connected to the unipolar atrial output of the pulse output circuits 56U which, via the atrial lead connector 48U, is connected to the tip electrode 34U of the bipolar atrial lead 32U. The other input to the P-wave sense/pace/capture amplifier 158 is connected to the switch 100 which selects either the unipolar atrial output of the pulse output circuits 56U which is connected to the direct electrical connection 70 to the pacemaker can 46, or the indifferent electrode 80.

When the switch 100 connects the other input of the P-wave sense/pace/capture amplifier 158 to the unipolar atrial output of the pulse output circuits 56U which is connected to the direct electrical connection 70 to the pacemaker can 46, the P-wave sense/pace/capture amplifier 158 acts as an atrial sense/pace amplifier. When the switch 100 connects the other input of the P-wave sense/pace/capture amplifier 158 to the indifferent electrode 80, the P-wave sense/pace/capture amplifier 158 acts as an atrial capture amplifier. The switch 100 is operated by a signal from the decoder and encoder 68.

Similarly, one of the inputs to the R-wave sense/pace/capture amplifier 162 is connected to the unipolar ventricular output of the pulse output circuits 56U which, via the ventricular lead connector 50U, is connected to the tip electrode 40U of the unipolar ventricular lead 38U. The other input to the R-wave sense/pace/capture amplifier 162 is connected to a switch 102 which selects either the unipolar ventricular output of the pulse output circuits 56U which is connected to the direct electrical connection 70 to the pacemaker can 46, or the indifferent electrode 80.

When the switch 102 connects the other input of the R-wave sense/pace/capture amplifier 162 to the unipolar ventricular output of the pulse output circuits 56U which is connected to the direct electrical connection 70 to the pacemaker can 46, the R-wave sense/pace/capture amplifier 162 acts as a ventricular sense/pace amplifier. When the switch 102 connects the other input of the R-wave sense/pace/capture amplifier 162 to the indifferent electrode 80, the R-wave sense/pace/capture amplifier 162 acts as a ventricular capture amplifier. The switch 102 is operated by a signal from the decoder and encoder 68.

The operation of the system of FIG. 15 is similar to that of FIG. 14. Following delivery of an atrial pacing pulse, the P-wave sense/pace/capture amplifier 158 will sense atrial capture during the absolute refractory period (approximately 100 milliseconds) which follows the atrial pacing pulse. Similarly, following delivery of a ventricular pacing pulse, the R-wave sense/pace/capture amplifier 162 will sense ventricular capture during the absolute refractory period (approximately 100 milliseconds) which follows the ventricular pacing pulse. In sensing capture, the system of FIG. 15 operates in a manner similar to the system of FIGS. 1 and 7.

Figure 16:
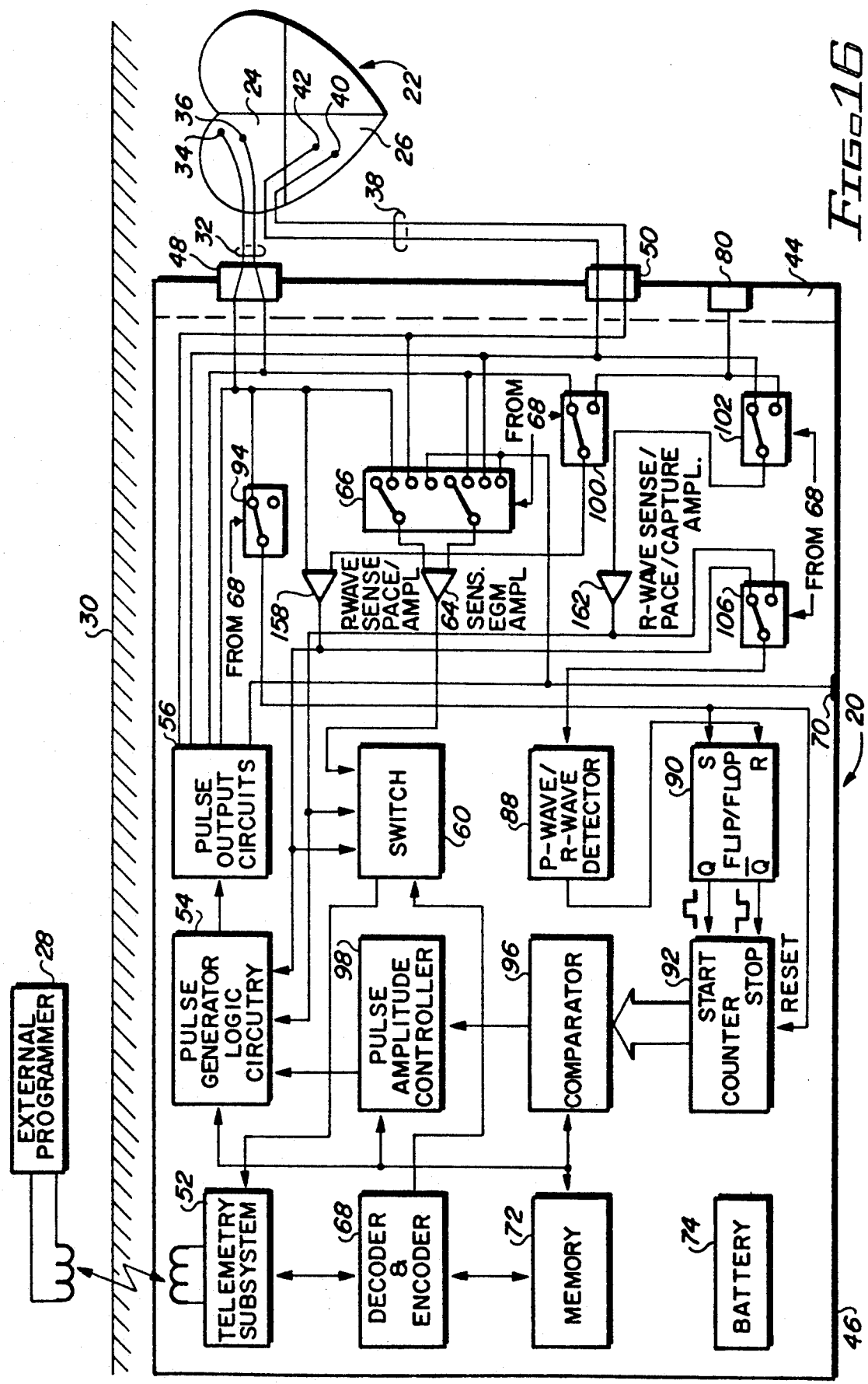
FIG. 16 is a schematic block diagram of a dual chamber, bipolar cardiac pacing system as shown in FIG. 14, additionally including means for automatically controlling the output pulse characteristics.

FIG. 16 is a bipolar system with automatic pulse amplitude (and/or pulse width) adjustment similar to FIG. 12, but with the P-wave sense/pace/capture amplifier 158 and the R-wave sense/pace/capture amplifier 162 of FIG. 14 used in place of the P-wave sense/pace amplifier 58 and the R-wave sense/pace amplifier 62, respectively. The output from the capture sense amplifier 76 in FIG. 12 as supplied to the P-wave/R-wave detector 88 is replaced by a signal from a switch 106, which selectively supplies one of two inputs to the P-wave/R-wave detector 88.

When the P-wave is to be detected by the P-wave/R-wave detector 88, the switch 106 supplies the output of the P-wave sense/pace/capture amplifier 158 to the P-wave/R-wave detector 88. Similarly, when the R-wave is to be detected by the P-wave/R-wave detector 88, the switch 106 supplies the output of the R-wave sense/pace/capture amplifier 162 to the P-wave/R-wave detector 88. The switch 106 is operated by a signal from the decoder and encoder 68.

Otherwise, the components and functions of FIG. 16 are identical to those in FIGS. 12 and 14, and similar reference numerals have been used. No further discussion of FIG. 16 is therefore believed to be necessary.

FIG. 17 is a unipolar system with automatic pulse amplitude (and/or pulse width) adjustment similar to FIG. 13, but with the P-wave sense/pace/capture amplifier 158 and the R-wave sense/pace/capture amplifier 162 of FIG. 15 used in place of the P-wave sense/pace amplifier 58 and the R-wave sense/pace amplifier 62, respectively. The output from the capture sense amplifier 76 in FIG. 13 as supplied to the P-wave/R-wave detector 88 is replaced by a signal from a switch 106, which selectively supplies one of two inputs to the P-wave/R-wave detector 88.

When the P-wave is to be detected by the P-wave/R-wave detector 88, the switch 106 supplies the output of the P-wave sense/pace/capture amplifier 158 to the P-wave/R-wave detector 88. Similarly, when the R-wave is to be detected by the P-wave/R-wave detector 88, the switch 106 supplies the output of the R-wave sense/pace/capture amplifier 162 to the P-wave/R-wave detector 88. The switch 106 is operated by a signal from the decoder and encoder 68.

Otherwise, the components and functions of FIG. 17 are identical to those in FIGS. 13 and 15, and similar reference numerals have been used. No further discussion of FIG. 17 is therefore believed to be necessary.

It should be recognized that although an implanted pacemaker has been shown in the figures for illustrative purposes, the invention is not limited to an implanted pacemaker. An external pacemaker may be provided in accordance with the teachings of the invention. The invention may also be used in pacing systems which may be incorporated with or used in combination with other electrical stimulation systems, such as cardioverter/defibrillator systems. In general, the subject matter disclosed herein may be used in any type of cardiac stimulation system wherein capture verification is desirable.

It may therefore be appreciated from the above detailed description of the preferred embodiment of the present invention that it teaches a system which is capable of reliably sensing capture, and that the system is capable of sensing capture on a continual basis. The system of the present invention is capable of sensing capture while pacing in a bipolar configuration with bipolar leads. It is also capable of reliably sensing capture in a unipolar pacing system having unipolar leads.

It is relatively simple to implement, and thus will not increase the size of the pacemaker. In addition, it will significantly extend the operating life of the pacer while constantly maintaining capture, thus benefiting the patient in two important ways. Finally, all of the aforesaid advantages and objectives are achieved without incurring any substantial relative disadvantage.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A cardiac pacing system, comprising:
    two pacing electrodes for use in pacing a heart, at least one of said two pacing electrodes being located on a pacing lead;
    cardiac pacing means connected to said two pacing electrodes for generating cardiac stimulation pulses, said pulses being delivered to cardiac tissue via said two pacing electrodes;
    an indifferent electrode;
    an amplifier for sensing cardiac signals, said amplifier for connection to said two pacing electrodes, said amplifier comprising means for disabling said amplifier from sensing signals between said two pacing electrodes during a predefined period of time following a stimulation pulse, said predetermined period of time being referred to as a refractory period; and
    means for verifying capture as a result of said stimulation pulses, said verifying means including means for switching one of the inputs to said amplifier from said one of said two pacing electrodes to said indifferent electrode during at least a portion of said refractory period, said amplifier functioning to sense capture during said at least a portion of said refractory period.

2. A system as defined in claim 1, further comprising:

means for controlling the energy content of said stimulation pulses of said cardiac pacing means in accordance with said verifying means, said means for controlling the energy content comprising means for reducing the energy content of said stimulation pulses until capture is lost and then increasing the energy content to a margin of safety above the minimum energy content necessary to retain capture.

3. A system as defined in claim 2, wherein said means for controlling the energy content of the stimulation pulses comprises:
   means for adjusting at least one of the amplitude or duration of said stimulation pulses.

4. A system for determining cardiac capture, comprising:
   first pulse generating means for generating stimulation pulses;
   a first electrical lead having a first electrically conductive electrode thereon, said first electrode for connection to said first pulse generating means for delivery of stimulation pulses from said first pulse generating means to said first electrode;
   first electrically conductive means spaced away from said first electrode for providing a return path for stimulation pulses from said first pulse generating means; and
   means for verifying cardiac capture as a result of the stimulation pulses from said first pulse generating means, said verifying means comprising:
      a capture sensing lead having an indifferent electrode mounted thereon, said indifferent electrode being spaced away from said first electrode and said first electrically conductive means, said first electrode and said indifferent electrode being used to sense capture.

5. A system for determining cardiac capture, comprising:
   first pulse generating means for generating stimulation pulses;
   a first electrical lead having a first electrically conductive electrode thereon, said first electrode for connection to said first pulse generating means for delivery of stimulation pulses from said first pulse generating means to said first electrode;
   first electrically conductive means spaced away from said first electrode for providing a return path for stimulation pulses from said first pulse generating means;
   an amplifier for sensing cardiac signals, said amplifier having a first input for connection to said first electrical lead and a second input for connection to said first electrically conductive means, said amplifier comprising means for disabling said amplifier from sensing signals between said first electrical lead and said first electrically conductive means during a predefined period of time following a stimulation pulse, said predetermined period of time being referred to as a refractory period; and
   means for verifying cardiac capture as a result of the stimulation pulses from said first pulse generating means, said verifying means comprising:
      an indifferent electrode spaced away from said first electrode and said first electrically conductive means; and
      means for switching said second input of said amplifier from said first electrically conductive means to said indifferent electrode during at least a portion of said refractory period, said amplifier functioning to sense capture during said at least a portion of said refractory period.

6. A method for determining capture of cardiac stimulation pulses, comprising the steps of:
   supplying a cardiac stimulation pulse to an electrode contained on a lead;
   providing a return path for stimulation pulses; and
   verifying cardiac capture as a result of the stimulation pulses from said first pulse generating means, said verifying step comprising:
      sensing the presence or absence of capture between said electrode on said lead and an indifferent electrode mounted on a capture sensing lead and spaced away from said first electrode.

7. A method for determining capture of cardiac stimulation pulses, comprising the steps of:
   supplying a cardiac stimulation pulse to an electrode contained on a first electrical lead;
   providing an electrically conductive return path for stimulation pulses; and
   sensing cardiac signals with an amplifier having a first input for connection to said electrode and a second input for connection to said electrically conductive return path, said amplifier being disabled from sensing signals between said electrode and said electrically conductive return path during a predefined period of time following a stimulation pulse, said predetermined period of time being referred to as a refractory period; and
   verifying cardiac capture as a result of the stimulation pulses, said verifying step comprising:
      switching said second input of said amplifier from said electrically conductive return path to said indifferent electrode during at least a portion of said refractory period, said amplifier functioning to sense the presence or absence of capture during said at least a portion of said refractory period.

* * * * *